United States Patent [19]

Tanaka et al.

[11] 4,328,295

[45] May 4, 1982

[54] SOLID ELECTROLYTE FOR USE IN OXYGEN CONCENTRATION SENSOR

[75] Inventors: Katsuhiko Tanaka, Toyokawa; Toshitaka Saito, Toyohashi; Masatoshi Suzuki, Anjo; Masami Ouki, Nagoya, all of Japan

[73] Assignee: Nippondenso Co., Ltd., Kariya, Japan

[21] Appl. No.: 231,843

[22] Filed: Feb. 5, 1981

[30] Foreign Application Priority Data

Feb. 7, 1980 [JP] Japan .................................. 55/14608

[51] Int. Cl.$^3$ ........................ C04B 35/48; H01M 6/18
[52] U.S. Cl. .................................. 429/193; 501/103; 204/195 S
[58] Field of Search ...................... 106/39.5, 73.2, 57; 252/62.2; 204/195 S; 429/30, 104, 193; 423/608, 266; 501/103

[56] References Cited

U.S. PATENT DOCUMENTS

| 3,301,646 | 1/1967 | Smoot | 106/57 |
|---|---|---|---|
| 3,432,314 | 3/1969 | Mazdiyasni et al. | 106/73.2 |
| 3,843,400 | 10/1974 | Radford et al. | 204/195 S |
| 4,170,531 | 10/1979 | Watanabe et al. | 204/195 S |
| 4,205,051 | 5/1980 | Takahashi et al. | 106/57 |
| 4,219,359 | 8/1980 | Miwa et al. | |

Primary Examiner—Edward J. Meros
Assistant Examiner—Mark Bell
Attorney, Agent, or Firm—Cushman, Darby & Cushman

[57] ABSTRACT

A solid electrolyte for an oxygen concentration sensor is provided by mixing $ZrO_2$ and about 7.5 to 8.5% by mol of a stabilizer such as $Y_2O_3$, grinding the mixture to have a BET specific surface are of about 9 to 20 m$^2$/g, adding to the ground mixture a forming aid, forming the mixture into a predetermined configuration and firing the formed mixture at about 1420° to 1520° C. The electrolyte has a surface-average grain size of about 5 microns or less and a structure of a cubic phase alone at the surface thereof and even in a finely ground state.

9 Claims, 5 Drawing Figures

SOLID ELECTROLYTE FOR USE IN OXYGEN CONCENTRATION SENSOR

BACKGROUND OF THE INVENTION

This invention relates to an oxygen sensor used in detecting the oxygen concentration in a gas such as the exhaust gas from an internal combustion engine of automotive vehicles. More particularly, it relates to a solid electrolyte consisting essentially of completely stabilized, sintered zirconia, which has a good thermal shock resistance.

Among the solid electrolytes of this sort for use in an oxygen sensor, there has been known a sintered body of stabilized zirconia which is prepared by mixing zirconia with a stabilizer such as yttria, calcia, or ytterbia followed by sintering at high temperatures, as disclosed in U.S. Pat. No. 4,219,359 (Miwa et al.).

A solid electrolyte made of the completely stabilized, sintered zirconia has such a defect that it exhibits a poor thermal shock resistance to a rapid change in temperature.

The inventors have discovered that this defect is predominently caused by the structural coarseness of the completely stabilized, sintered zirconia crystals.

SUMMARY OF THE INVENTION

Accordingly, the object of the present invention is to maintain a surface-average grain size in the structure of the completely stabilized, sintered zirconia at about 5 microns or less, thereby to provide a solid electrolyte for use in an oxygen concentration sensor having an excellent thermal shock resistance.

Other objects and features of this invention will become apparent from the following descriptions.

DESCRIPTION OF THE INVENTION AND THE PREFERRED EMBODIMENTS

In this invention, the "completely stabilized, sintered zirconia" is literally completely stable and, hence, even when it was pulverized, the X-ray diffraction analysis shows a cubic phase alone.

According to this invention, in order to obtain the completely stabilized, sintered zirconia constituted by the cubic phase alone, the concentration of a stabilizer such as yttria should be selected, for example, within the range of from about 7.5 to 8.5% by mol (the remainder being zirconia), and the sintering temperature should be properly selected, i.e., within the range of from about 1420° to 1520° C.

Furthermore, in order to maintain the surface-average particle size at about 5 microns or less, the sintering temperature or the concentration of a stabilizer such as yttria may be changed.

The technical-grade zirconia being used as a raw material in manufacturing the solid electrolyte of this invention contains, as a rule, certain amounts of impurities such as hafnium oxide, titanium oxide, iron oxide, and so on. Therefore, the constituents of the completely stabilized, sintered zirconia of this invention are permitted to contain the above-noted impurities.

Furthermore, in preparing the sintered zirconia according to this invention, a sintering promoter such as aluminum oxide and/or silicon oxide can be used. The suitable amount added of a promoter ranges from about 1 to 5% by weight for aluminum oxide and from about 0.2 to 2% by weight for silicon oxide, said amounts being based on the total weight of zirconia and the stabilizer such as yttria.

An example of the structure of an oxygen sensor employing the solid electrolyte of this invention is described below by referring to the accompanying drawings.

Figure 5:
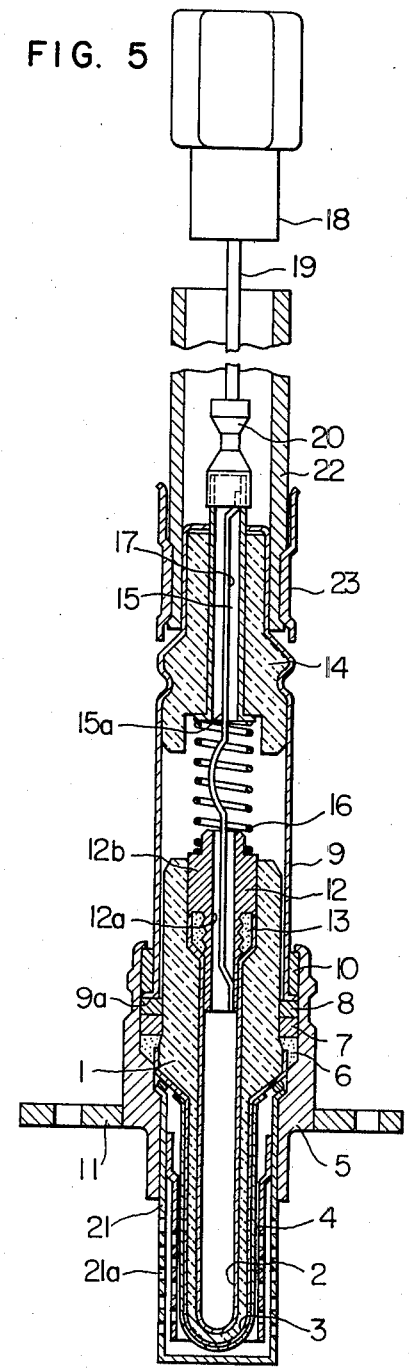
FIG. 5 is a partial sectional view illustrating one example of the construction of an oxygen sensor employing the solid electrolyte of this invention.

In FIG. 5, 1 is an oxygen concentration detecting element formed from the solid electrolyte comprising about 92% by mol of zirconia and about 8% by mol of yttria in the form of solid solution. The element 1, in a cup-like form open at one end and closed at the other, is coated on inner and outer surfaces with porous layers of the first electrode 2 and the second electrode 3, which are composed of platinum and are applied by chemical plating, vacuum deposition or paste baking. The second electrode is covered with a heat-resistant porous protective coating of metal oxides such as magnesia-alumina spinel ($MgAl_2O_4$) and the like, in the area where it is exposed to the exhaust gas. Tubular housing 5 made of a heat-resistant metal is provided around the outer surface of the oxygen concentration detecting element 1. In the annular space between the housing 5 and the oxygen concentration detecting element 1, there are disposed conductive graphite powder 6, absestos ring 7, and conductive metallic ring 8. One end of protective tube 9 made of a conductive heat-resistant metal, e.g. stainless steel, is inserted into said annular space. This end of the protective tube 9 carries spacer ring 10 of a conductive metal supported on flange 9a. The upper edge of housing 5 is fixed to the protective tube 5 by calking to hold in place both the housing 5 and the protective tube 9 against the oxygen concentration detecting element 1. The housing 5 is provided with flange 11 to fix the device to the exhaust line (not shown). The area of the outer surface of oxygen concentration detecting element 1, where it is not exposed to the exhaust gas, is covered with a portion of the protective tube 9, as mentioned above. Stem 12, made of a conductive metal, e.g. stainless steel, and having through-hole 12a along the center line, is fixed, through conductive graphite powder 13, to the inner wall of the oxygen concentration detecting element 1. Insulator 14 of alumina or the like is disposed in the upper end portion of the protective tube 9 and held in place by calking the upper edge of the protective tube. Hollow tube 15 made of a conductive metal, e.g. stainless steel, is inserted through the insulator 14 and spring 16 is mounted between the flange 15a of tube 15 and the shoulder 12a formed in the stem 12. The stem 12 is tightly fixed in place by being pressed against the oxygen concentration detecting element 1 by the pressure exerted from the set load of the spring 16. A piece of stainless steel wire 17 is fixed by welding at one end thereof to the wall of through-hole 12a of the stem 12 and welding at the other end to the upper inside wall of hollow tube 15. A leading wire 19 from connector 18 is connected to the end of the hollow tube 15 opposite to the flange 15a by calking the terminal piece 20. A duplex protective tube 21 having a large number of small holes 21a is fixed to the lower end of housing 5 so as to cover the area of outer surface of the oxygen concentration detecting element 1, where it is exposed to the exhaust gas. The first electrode 2 of the oxygen concentration detecting element 1 is electrically connected to the leading wire 19 through the graphite powder 13, stem 12, stainless steel wire 17, and hollow tube 15 or intervening spring 17. The second electrode 3 is electrically connected to the housing 5 through the conductive graphite powder 6 and conductive ring 8. Heat-resistant rubber tubing 22 is fitted around the protective tube 9 through the intervening collar 23.

The invention is illustrated below in detail with reference to Example in which yttrium oxide was used as the stabilizer, through other metallic oxides such as, for example, calcium oxide, magnesium oxide, scandium oxide and ytterbium oxide may be used.

EXAMPLE

Commercially available zirconium oxide of about 99.5% in purity, containing a small amount of hafnium oxide ($HfO_2$) and having a BET specific surface area of about 2.5 $m^2/g$ was blended with commercially available yttrium oxide of about 99.9% in purity, having a BET specific surface area of about 3.8 $m^2/g$, in predetermined molar ratios as shown in Table 1. The resulting mixture was ground so as to obtain a powder having a specific surface area of 12 $m^2/g$. The powdered mixture was mixed with a forming aid such as polyvinyl alcohol or the like to form a slurry containing about 40 to 45% by weight of water. The slurry was spray-dried and molded into a rectangular, disc or tubular specimen by means of an oil press at a pressure of 1 ton/$cm^2$. Each specimen was fired at a predetermined temperature, as shown in Table 1, for 3 hours under an oxidizing atmosphere at a normal pressure. The fired rectangular specimen was tested for the flexural strength, stability of structure, and surface-average grain size by the methods described later. The specimen in a disc form was polished to obtain a mirror-finished surface and the monoclinic phase content of the surface was determined; the monoclinic phase content of the pulverized specimen was also determined. Another disc specimen was ground to a thickness of about 2.5 microns, then coated on both sides with a silver paste in a circular area of about 200 mm in diameter, and baked. The disc thus treated was tested for the resistance at a temperature of about 400° C. and a constant current of 10 $\mu A$ (measurement was made after the lapse of about 10 minutes from the time when the temperature reached about 400° C. and the electric current was turned on). The tubular specimen was evaluated for the thermal shock resistance according to the methods and test conditions as described below.

The procedures and conditions of each test were as described below.

(a) Flexural strength: A sintered body was cut and ground to a rectangular rod of 5×8×60 mm in size and tested for the flexural strength by the known three-point bending test method.

(b) Stability of structure: After heating a rectangular sintered body at 200°±15° C. for 1000 hours, the fracture was examined by a scanning electron microscope (SEM) at 10,000 magnifications to determine the presence or absence of intergranular rupture caused by volume expansion originated from the phase transition.

(c) Monoclinic component content: A sintered body was finely pulverized to a particle size below 10 microns, whereby, if a tetragonal phase was present in the sintered body, the tetragonal phase was completely transformed into a monoclinic phase and the monoclinic component content was calculated by the equation:

$$\{I[M(11\bar{1})] + M(111)]/I[M(11\bar{1}) + M(111) + C(111)]\} \times 100 = \text{Weight \% monoclinic.}$$

When a tetragonal phase is detected at the surface or lapped surface of the sintered body, there arises a question whether or not the tetragonal phase is completely eliminated on pulverizing. With this respect, it was confirmed that after pulverization no X-ray diffraction peak of the tetragonal phase was found, under the following conditions, in the sample containing initially a tetragonal phase, indicating that the phase transition had been completed. In the above equation M and C represent monoclinic and cubic phases, respectively. The X-ray diffraction intensity I is a value integrated by peak-height×half-width.

| Conditions for X-ray diffraction: | |
|---|---|
| Target: | (Rotary type) Cu |
| Tube voltage: | 40 kV |
| Tube current: | 80 mA |
| Divergency slit: | 1° |
| Receiving slit: | 1 mm |
| Goniometer speed: | $2\theta - 1°$/minute |
| Chart speed: | 20 mm/minute |
| Time constant: | 1 second |
| Full scale: | 4,000 cps–400 cps |
| Provided with graphite monochrometer Limit of detection for monoclinic | |
| phase: | > 0.5 weight % |

Figure 1:
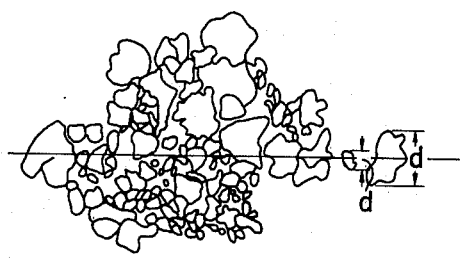
FIG. 1 is a schematic drawing to illustrate the method employed in this invention for measuring the surface-average particle size.

(d) Surface-average grain size: The surface-average grain size was determined on the SEM photograph of the sintered body surface taken at 1,000–10,000 magnifications. A straight line was drawn at random across the photograph, as shown schematically in FIG. 1. The diameter of each of the grains lying across the line was determined in terms of the maximum width (d in FIG. 1) of the grain measured in the direction vertical to said straight line. Another straight line was drawn parallel to the above line with a sufficient space therebetween so as not to cross over the grains which had already been measured and the diameter determination was repeated on all the grains lying across the straight line. The determination ws further repeated until the number of measured grains had amounted to 20–50. The average value of the determined diameters was taken as a surface-average grain size.

Figure 2:
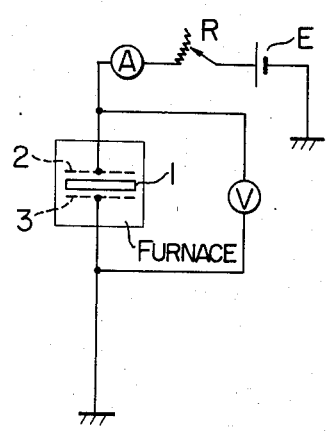
FIG. 2 is an electric connecting diagram to illustrate the method employed in this invention for measuring the resistance.

(e) Resistance: The disc specimen 1 provided with silver electrodes 2 and 3, as shown above, was connected to a circuit shown in FIG. 2 and the resistance R was determined under a constant current load. In FIG. 2, A is an ammeter, V a voltmeter, R a rheostat, and E an electric source.

(f) Thermal shock resistance: The aforesaid tubular specimen of the sintered body was a tube closed at one end having an inner diameter of 4 mm and an outer diameter of 8 mm, which was prepared by molding a granulated material by means of a common hydrostatic press at a pressure of 1 ton/$cm^2$, followed by baking. Inside the closed end of the tubular sintered body, was placed the heat sensing junction of a CA thermo-couple which was connected to a recorder to record the temperature with the lapse of time, whereby the rate of increase or decrease of temperature (°C./second) could be calculated. The relative position of a burner to the zirconia sintered body was adjusted so that the flame of the burner supplied with a mixed fuel gas of compressed air and a city gas could touch the zirconia sintered body at the closed end and over a length of about 1.5 mm measured from the closed end. The recorder operated simultaneously with the lighting of the fuel gas to determine the rate of temperature change. After this thermal shock test, the cooled zirconia sintered body was dyed with fuchsine to examine the cracking and the rate of temperature increase which caused the cracking was determined for each of the zirconia sintered bodies prepared under various conditions. The higher the rate of temperature change which caused cracking, the higher the thermal shock resistance was rated.

The results obtained in the example were as shown in Table 1.

TABLE 1

Results of evaluation obtained in Example.

| Test No. | $Y_2O_3$ concentration (mole-%) | Sintering temperature (°C.) | Bulk specific gravity after sintering (in Hg) | Flexural strength (kg/mm$^2$) | Stability of structure (intergranular rupture) |
|---|---|---|---|---|---|
| 1 | 5 | 1520 | 5.69 | 28.6 | Yes |
| 2 |   | 1720 | 5.72 | 37.5 | ↑ |
| 3 | 6 | 1520 | 5.65 | 25.9 | ↑ |
| 4 |   | 1720 | 5.67 | 27.5 | ↑ |
| 5 | 7.5 | 1520 | 5.68 | 25.9 | No |
| 6 |   | 1720 | 5.70 | 14.7 | ↑ |
| 7 | 8.0 | 1470 | 5.67 | 19.0 | ↑ |
| 8 |   | 1720 | 5.72 | 14.5 | ↑ |
| 9 | 8.5 | 1420 | 5.64 | 20.1 | ↑ |
| 10 |   | 1720 | 5.64 | 15.1 | ↑ |
| 11 | 9.0 | 1420 | 5.60 | 16.9 | ↑ |
| 12 |   | 1720 | 5.64 | 14.8 | ↑ |
| 13 | 10 | 1520 | 5.54 | 15.2 | ↑ |
| 14 |   | 1720 | 5.56 | 14.0 | ↑ |
| 15 | 11 | 1520 | 5.48 | 14.5 | ↑ |
| 16 |   | 1720 | 5.51 | 14.2 | ↑ |

| Test No. | Monoclinic content Surface (wt.-%) | Monoclinic content Powder (wt.-%) | Surface-average grain size (microns) | Resistance (kΩ) | Thermal shock resistance (°C./sec.) |
|---|---|---|---|---|---|
| 1 | 17 | 21 | 0.9 | 7.9 | >60 |
| 2 | 3.5 | 8.2 | 5.4 | 7.2 | >45 |
| 3 | 4.8 | 7.4 | 1.2 | 5.9 | >50 |
| 4 | Not detected | 5.5 | 9.5 | 6.4 | >40 |
| 5 | ↑ | Not detected | 1.2 | 1.9 | >40 |
| 6 | ↑ | ↑ | 34.0 | 5.7 | >25 |
| 7 | ↑ | ↑ | 2.2 | 3.3 | >30 |
| 8 | ↑ | ↑ | 35.4 | 4.2 | >20 |
| 9 | ↑ | ↑ | 4.9 | 7.2 | >30 |
| 10 | ↑ | ↑ | 32.4 | 10.2 | >20 |
| 11 | ↑ | ↑ | 7.2 | 14 | >25 |
| 12 | ↑ | ↑ | 38.8 | 17 | >20 |
| 13 | ↑ | ↑ | 13.0 | 22 | >25 |
| 14 | ↑ | ↑ | 37.5 | 26 | >20 |
| 15 | ↑ | ↑ | 9.6 | 29 | >25 |
| 16 | ↑ | ↑ | 40.1 | 32 | >20 |

As is seen from Table 1, test Nos. 5 to 16 represent sintered bodies of completely stabilized zirconia in which no monoclinic phase can be seen in the surfaces of said bodies or even when said bodies were pulverized, i.e., a cubic phase only was detected. Test Nos. 5, 7 and 9 all had a good thermal shock resistance and a low electric resistance. Furthermore, in these tests, no intergranular rupture was seen. The bodies of test Nos. 5, 7 and 9 were found to have surface-average particle sizes of 1, 2, 2.2 and 4.9 microns, respectively, which are very small.

On the other hand, test Nos. 6, 8 and 10 to 16 all had a poor thermal shock resistance, a high electric resistance and a low flexural strength. The bodies of these tests were found to have a considerably greater surface-average particle size.

Figure 3:
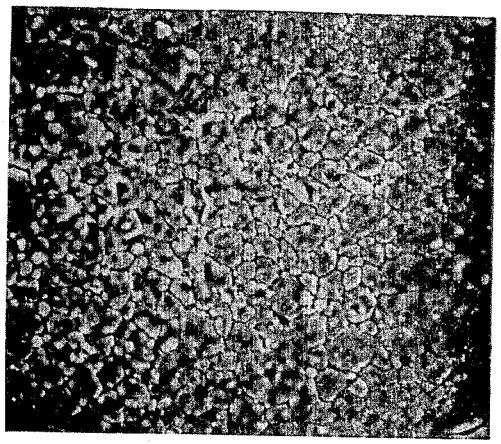
FIGS. 3 and 4 are microphotographs of a solid electrolyte to illustrate the invention.
Figure 4:
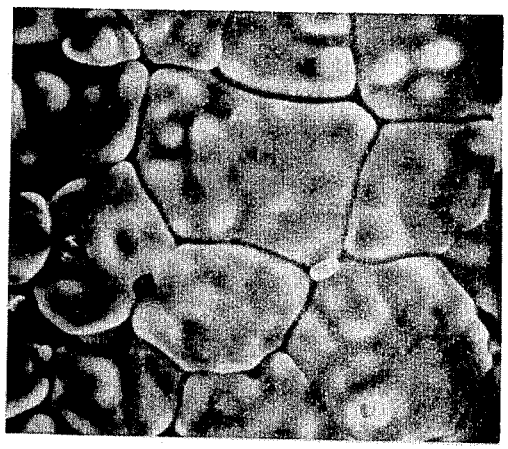

A SEM photograph of the surface of the test No. 7 body is shown in FIG. 3 and that of test No. 13 body shown in FIG. 4. The SEM magnifications are 2,000 and hence a length of 20 mm in an actual scale on the photographs corresponds to 10 microns.

In test Nos. 1 to 3, a monoclinic phase was seen both in the surfaces of the sintered bodies and when said bodies were pulverized. These bodies were found to lack the stability of structure due to a great amount of the monoclinic phase. As to test No. 4, the monoclinic phase was observed only when the sintered body was pulverized. This sintered body was also found to lack the stability of structure due to a great amount of the monoclinic phase.

From the results shown in table 1, it has been found that in order to obtain a sintered body of zirconia having an excellent thermal shock resistance and a low electric resistance, it is necessary to maintain the surface-average particle size of a sintered body at a range of up to about 5 microns.

As fully mentioned above, the solid electrolyte according to this invention can have an improved thermal shock resistance and an excellent oxygen ion conductivity. Thus, this invention may provide an oxygen sensing solid electrolyte suitable for practical use.

What is claimed is:

1. A solid electrolyte for an oxygen concentration sensor, consisting essentially of a sintered body of completely stabilized zirconia having a crystal structure of a cubic phase alone and having a surface-average grain size of about 5 microns or less, said sintered body having a cubic phase alone even in a finely ground state.

2. The solid electrolyte according to claim 1, wherein the sintered body contains $Y_2O_3$ as a stabilizer.

3. The solid electrolyte according to claim 1, wherein the sintered body contains CaO as a stabilizer.

4. The solid electrolyte according to claim 1, wherein the sintered body contains MgO as a stabilizer.

5. The solid electrolyte according to claim 1, wherein the sintered body contains $Yb_2O_3$ as a stabilizer.

6. The solid electrolyte according to claim 1, wherein the sintered body contains $Sc_2O_3$ as a stabilizer.

7. The electrolyte according to claim 2, 3, 4, 5 or 6, wherein the stabilizer is contained in an amount of about 7.5 to 8.5% by mol.

8. The electrolyte according to claim 2, 3, 4, 5 or 6, wherein the sintered body contains as a sintering promotor about 1 to 5% by weight of $Al_2O_3$ or about 0.2 to 2% by weight of $SiO_2$, both the percentages being based on the total of $ZrO_2$ and the stabilizer.

9. A solid electrolyte for an oxygen concentration sensor, consisting essentially of a sintered body of completely stabilized zirconia and from about 7.5 to about 8.5 mol percent of a zirconia stabilizer, said zirconia having a crystal structure of a cubic phase alone and having a surface-average grain size of about 5 microns or less, said sintered body having a cubic phase alone even in a finely ground state.

* * * * *